| United States Patent [19] | [11] | 4,405,808 |
|---|---|---|
| Nakajima et al. | [45] | Sep. 20, 1983 |

[54] PROCESS FOR PREPARING ACETIC ACID ESTERS

[75] Inventors: Kazuhisa Nakajima, Minoo; Masahiko Miyashita, Takatsuki; Susumu Hakozaki, Hirakata; Yoshinori Chosakon, Ibaraki, all of Japan

[73] Assignee: Nippon Gohsei Kagaku Kogyo Kabushiki Kaisha, Osaka, Japan

[21] Appl. No.: 370,037

[22] Filed: Apr. 20, 1982

[30] Foreign Application Priority Data

Apr. 24, 1981 [JP] Japan .................................. 56-63086
Apr. 30, 1981 [JP] Japan .................................. 56-66601

[51] Int. Cl.$^3$ .............................................. C07C 67/04
[52] U.S. Cl. .................................................. 560/247
[58] Field of Search ........................................ 560/247

[56] References Cited

U.S. PATENT DOCUMENTS 3,932,306   1/1976   Rona .................................. 560/247

FOREIGN PATENT DOCUMENTS 1446964   8/1976   United Kingdom .

Primary Examiner—Michael L. Shippen
Attorney, Agent, or Firm—Armstrong, Nikaido, Marmelstein & Kubovcik

[57] ABSTRACT

A process for preparing acetic acid ester by reacting acetic acid with an aliphatic lower olefin in vapor phase in the presence of steam and a catalyst selected from aromatic disulfonic acids and their esters. The high activity of the catalyst can be maintained and the product is obtained in a high space time yield by the presence of steam in the reaction. The effect of maintaining the high activity can be further increased by using silica treated with a strong acid as a carrier.

5 Claims, No Drawings

PROCESS FOR PREPARING ACETIC ACID ESTERS

BACKGROUND OF THE INVENTION

The present invention relates to a process for preparing acetic acid esters by a vapor phase reaction, and more particularly to a process for the preparation of acetic acid esters by the reaction of acetic acid and aliphatic lower olefins, especially the preparation of ethyl acetate by the reaction of acetic acid and ethylene.

Processes for preparing carboxylic acid esters from olefins and carboxylic acids are carried out in the vapor phase or liquid phase. In the vapor phase reaction, an olefin gas is reacted with acetic acid vapor in the presence of a catalyst. The vapor phase reaction is advantageous in that the reaction is carried out under mild conditions without employing a reaction medium.

There are many reports on the catalysts used in the vapor phase reaction of olefins and carboxylic acids to produce the corresponding carboxylic acid esters, e.g. catalysts such as sulfuric acid, ethylsulfuric acid and diethylsulfate. Japanese Unexamined Patent Publication (Tokkyo Kokai) No. 46587/1975 discloses aromatic disulfonic acid catalysts such as benzenedisulfonic acid. These aromatic disulfonic acid catalysts are advantageous of high activity and low corrosiveness to apparatuses in comparison with the other known catalysts. However, these catalysts exhibit high activity only in a short period of reaction time. That is to say, though the catalyst activity is high in the initial stage of the reaction and carboxylic acid esters can be produced in a high space time yield, the activity is gradually lowered with the progress of the reaction. Thus, the aromatic disulfonic acid catalysts must be improved for the industrial preparation of carboxylic acid esters.

It is an object of the present invention to provide a process for preparing a carboxylic acid ester by the reaction of a carboxylic acid and an olefin in vapor phase.

A further object of the invention is to provide a process for preparing an acetic acid ester by the reaction of acetic acid and an olefin in vapor phase in the presence of a catalyst.

A still further object of the invention is to provide a process for preparing an acetic acid ester in high yields over a long period of time.

These and other objects of the invention will become apparent from the description hereinafter.

SUMMARY OF THE INVENTION

It has now been found that the above-mentioned objects can be attained by reacting acetic acid and an aliphatic lower olefin in vapor phase in the presence of steam on a catalyst, i.e. aromatic disulfonic acids and/or their esters.

In accordance with the present invention, there is provided a process for preparing an acetic acid ester which comprises reacting acetic acid and an aliphatic lower olefin in vapor phase in the presence of steam on a catalyst selected from the group consisting of aromatic disulfonic acids and esters thereof.

DETAILED DESCRIPTION

The feature of the present invention is to maintain the high activity of the above-mentioned catalyst over a long period of reaction time by supplying steam to the reaction system at the time of reacting acetic acid and an aliphatic lower olefin in the vapor phase. Such an effect produced by the presence of steam is remarkably exhibited only in the case using the specified catalyst, i.e. aromatic disulfonic acids and/or their esters. Even in the case using other known catalysts such as sulfuric acid, the presence of steam contributes to maintaining the catalyst activity somewhat, but the effect is not so remarkable as that of the present invention. Moreover, there is the case where the activity of the catalyst is rather hindered by the presence of steam depending on the kind of the catalyst and the amount of the steam. The aromatic disulfonic acids and/or their esters used as catalysts in the present invention show a peculiar behavior. It has not hitherto been attempted to positively make steam exist in the reaction system upon the preparation of acetic acid esters by the vapor phase reaction of acetic acid and an olefin. Further, the process of the present invention has the advantage that the corrosion of an apparatus which is unavoidable in the vapor phase reaction using a strong acid catalyst can be greatly decreased.

The aliphatic lower olefins to be reacted with acetic acid in the present invention include, for instance, ethylene, propylene, butene, and the like. The process of the invention is particularly suitable for the preparation of ethyl acetate from acetic acid and ethylene and the preparation of isopropyl acetate from acetic acid and propylene.

Typical examples of the aromatic disulfonic acid used as a catalyst in the present invention are benzene-1,2-disulfonic acid, benzene-1,3-disulfonic acid, benzene-1,4-disulfonic acid, naphthalene-1,5-disulfonic acid, naphthalene-2,6-disulfonic acid, naphthalene-2,7-disulfonic acid, and the like. Benzene-1,3-disulfonic acid and naphthalene-2,6-disulfonic acid are particularly preferred. The benzene ring or naphthalene ring of the aromatic disulfonic acid may be substituted by halogen atom. Typical examples of the halogen substituted aromatic disulfonic acid are 4-chlorobenzene-1,3-disulfonic acid, 4-fluorobenzene-1,3-disulfonic acid, 4-bromobenzene-1,3-disulfonic acid, 4,6-dichlorobenzene-1,3-disulfonic acid, 2,5-dichlorobenzene-1,3-disulfonic acid, 2,4,6-trichlorobenzene-1,3-disulfonic acid, 3-chloronaphthalene-2,6-disulfonic acid, and the like. The esters of the aromatic disulfonic acid are also effective as a catalyst. In case of using the esters, it is desirable to use the esters corresponding to the kind of the used olefin, in other words, the kind of the desired acetic acid ester product. For instance, in case of using ethylene as a raw material, ethyl esters of the aromatic disulfonic acids are preferably used. These catalyst may be used alone, or in admixture thereof, i.e. combination of the acids, combination of the esters or combination of the acid and the ester.

The catalyst is supported on a suitable carrier, e.g. silica and silica-alumina. Silica having a specific surface area of 100 to 300 m.$^2$/g. and an alumina content of not more than 5% by weight is preferably employed as a carrier. A manner of supporting the catalyst is not particularly limited, and any known manners are adoptable. Usually, the catalyst is supported by impregnating a carrier in an aqueous or acetic acid solution of an aromatic disulfonic acid and/or an ester thereof.

The amount of the aromatic disulfonic acid supported on a carrier is from 1.0 to 3.0 milligram equivalent in terms of sulfonic acid group, per gram of the carrier-supported catalyst.

The high activity of the catalyst can be more effectively maintained by using the silica carrier treated with a strong acid. The strong acid used for this purpose includes, for instance, inorganic acids such as sulfuric acid, hydrochloric acid and phosphoric acid, and organic acids such as benzenemonosulfonic acid, benzenedisulfonic acid, naphthalenedisulfonic acid and naphthalenetrisulfonic acid. The acid treatment may be carried out by any conventional methods, e.g. a method where silica carrier is added to a strong acid and agitated, and a method where silica carrier is packed in a tube or a cylinder and a strong acid is poured from the top of the tube or cylinder. The acid treatment is usually carried out by impregnating the silica carrier in a strong acid, heating for 5 to 20 hours at a temperature of 100° to 200° C., cooling, washing sufficiently with water and drying the carrier at an elevated temperature under a reduced pressure.

The reaction of acetic acid and an aliphatic lower olefin can be carried out by conventional reaction systems such as fixed bed system and fluid bed system. The acetic acid vapor, the olefin gas and steam are introduced continuously or intermittently to a reactor in which the aromatic disulfonic acid catalyst is packed. If necessary, an inert gas may also be introduced. The concentration of acetic acid is from 5 to 30% by volume, preferably 6 to 20% by volume, of the total amount of acetic acid and the olefin. The olefin/acetic acid ratio is from 3/1 to 20/1 by mole. The mixed gas is passed through the reactor at a space velocity of 300 to 5,000 Nl/liter of catalyst/hour, preferably 500 to 2,000 Nl/liter of catalyst/hour.

Steam is fed to a reactor in an amount of 0.3 to 15% by weight, preferably 0.5 to 10% by weight, based on the fed acetic acid. When the amount of steam is less than 0.3% by weight, the high activity of the catalyst cannot be maintained over a long period of time. When the amount of steam is more than 15% by weight, the activity of the catalyst itself is decreased even in the initial stage of reaction.

The reaction is carried out at a temperature of from 130° to 200° C., preferably from 160° to 180° C., under a pressure of from atmospheric pressure to 20 kg./cm.$^2$G, preferably from 3 to 15 kg./cm.$^2$G.

The reacted gas released from the reactor is condensed, and the desired product is isolated in a usual manner such as distillation or extraction.

The process of the present invention is more specifically described and explained by means of the following Examples, in which all % are by weight unless otherwise noted. It is to be understood that the present invention is not limited to the Examples and various changes and modifications may be made in the invention without departing from the spirit and scope thereof.

EXAMPLE 1

A stainless steel tubular reactor having an inner diameter of 22 mm. and a length of 780 mm. was packed with 80 ml. of a catalyst containing benzene-1,3-disulfonic acid supported on a silica carrier in an amount of 2 milligram equivalent in terms of sulfonic acid group per gram of the supported catalyst. The reactor was heated to 165° C., and at that temperature the reaction was carried out by feeding a mixture of ethylene gas, acetic acid vapor and steam from top of the reactor under a pressure of 6 kg./cm.$^2$G at a space velocity of 850 Nl/liter of catalyst/hour. The concentration of acetic acid was 10% by volume based on the total volume of acetic acid and ethylene. The amount of the fed steam was 2% based on the fed acetic acid. The gas passed through the reactor was condensed, and the obtained liquid was analyzed by gas chromatography to determine the space time yield of the produced ethyl acetate with the lapse of time.

The average space time yields obtained between 0 and 2 hours (hereinafter referred to as "STY-I"), between 22 and 24 hours (hereinafter referred to as "STY-II"), and between 46 and 48 hours (hereinafter referred to as "STY-III") were as follows:

STY-I: 177 g./l-cat.hr.
STY-II: 147 g./l-cat.hr.
STY-III: 132 g./l-cat.hr.

From the above result, it would be understood that the high activity of the catalyst is maintained for a long period of time.

COMPARATIVE EXAMPLE 1

The procedure of Example 1 was repeated except that steam was not fed.

STY-I, STY-II and STY-III were 185 g./l-cat.hr., 88 g./l-cat.hr. and 55 g./l-cat.hr., respectively, and the lowering of the catalyst activity was remarkable.

COMPARATIVE EXAMPLE 2

The reaction was carried out in the same manner as in Example 1 except employing sulfuric acid supported on a silica at 165° C. under a pressure of 2 kg./cm.$^2$G at a space velocity of 800 Nl/l-cat.hr.

STY-I, STY-II and STY-III were 200 g./l-cat.hr., 41 g./l-cat.hr. and 28 g./l-cat.hr., respectively.

EXAMPLES 2 TO 5

The reaction was carried out in accordance with the procedure of Example 1 under the conditions shown in Table 1.

The results are shown in Table 1.

TABLE 1

| Ex. No. | Olefin | Catalyst* | Amount of steam (% based on acetic acid) | Reaction pressure (kg./cm.$^2$G) | Reaction temperature (°C.) | STY (g./l-cat · hr.) I | II | III |
|---|---|---|---|---|---|---|---|---|
| 2 | Ethylene | BDS | 4 | 6 | 165 | 159 | 159 | 157 |
| 3 | Ethylene | BDS | 10 | 6 | 165 | 111 | 110 | 110 |
| 4 | Ethylene | BDSE | 2 | 6 | 165 | 185 | 155 | 135 |
| 5 | Ethylene | NDS | 2 | 6 | 165 | 132 | 110 | 100 |

(Note)
*Catalyst is supported on silica in an amount of 2 milligram equivalent per gram of supported catalyst.
BDS: Benzene-1,3-disulfonic acid
BDSE: Diethyl benzene-1,3-disulfonate
NDS: Naphthalene-2,6-disulfonic acid

EXAMPLE 6

The procedure of Example 1 was repeated except that 60 Nl/hr. of propylene, 29 ml/hr. of acetic acid and 0.46 g./hr. of water were passed through the reactor at 147° C. under a pressure of 2 kg./cm.$^2$G.

The space time yield of the produced isopropyl acetate between 0 and 2 hours was 262 g./l-cat.hr. The average space time yield between 0 and 6 hours was 253 g./l-cat.hr. and the catalyst activity was high. Also, the average conversion of acetic acid was 30%.

EXAMPLE 7

There were admixed 13 g. of sulfuric acid, 30 g. of water and 50 g. of silica, and after drying the silica, it was heated at 165° C. for 18 hours. The silica was then cooled, washed sufficiently with water and dried at 100° C. for 2 hours.

Benzene-1,3-disulfonic acid was supported on the thus acid-treated silica in an amount of 2 milligram equivalent in terms of sulfonic acid group per gram of supported catalyst.

The procedure of Example 1 was repeated except that the above catalyst was employed. The average space time yields between 0 and 2 hours (STY-I), between 22 and 24 hours (STY-II) and between 40 and 48 hours (hereinafter referred to as "STY-IV") were as follows:

STY-I: 190 g./l-cat.hr.
STY-II: 164 g./l-cat.hr.
STY-IV: 153 g./l-cat.hr.

EXAMPLES 8 TO 11

The procedure of Example 7 was repeated except that the catalyst and acid for treating the silica carrier shown in Table 2 were employed.

The results are shown in Table 2.

TABLE 2

| Ex. No. | Silica-supported catalyst | | STY (g./l-cat · hr.) | | |
|---|---|---|---|---|---|
| | Catalyst | Strong acid used in treatment of silica | I | II | IV |
| 8 | BDS | Hydrochloric acid | 184 | 161 | 158 |
| 9 | BDS | Benzene-1,3-disulfonic acid | 184 | 163 | 150 |
| 10 | BDSE | Sulfuric acid | 190 | 163 | 156 |
| 11 | NDS | Sulfuric acid | 151 | 137 | 132 |

What we claim is:

1. A process for preparing an acetic acid ester which comprises reacting acetic acid and an aliphatic lower olefin in vapor phase in the presence of steam on a catalyst selected from the group consisting of an aromatic disulfonic acid and an ester thereof.

2. The process of claim 1, wherein the amount of the steam is from 0.3 to 15% by weight based on the fed acetic acid.

3. The process of claim 1, wherein the catalyst is supported on a silica carrier treated with a strong acid.

4. The process of claim 1, wherein said aromatic disulfonic acid is benzenedisulfonic acid or naphthalenedisulfonic acid.

5. The process of claim 1, wherein said aliphatic lower olefin is an olefin having 2 to 4 carbon atoms.

* * * * *